United States Patent [19]

Chang et al.

[11] Patent Number: 4,774,175

[45] Date of Patent: Sep. 27, 1988

[54] IMMUNOCHEMICAL METHODS FOR THE DETECTION OF ANTIBODY AGAINST HTLV-III

[75] Inventors: Tse W. Chang, Paoli; Ikunoshin Kato, Exton; Pranab Chanda; Nancy T. Chang, both of Paoli, all of Pa.

[73] Assignee: Centocor, Inc., Malvern, Pa.

[21] Appl. No.: 707,066

[22] Filed: Mar. 1, 1985

[51] Int. Cl.$^4$ .................. C12Q 1/70; G01N 33/544
[52] U.S. Cl. .......................... 435/5; 435/7; 435/180; 435/805; 436/518; 436/528; 436/531; 436/811; 530/324
[58] Field of Search .......... 435/5, 7, 180, 805; 530/324; 436/518, 528, 531, 811

[56] References Cited

U.S. PATENT DOCUMENTS 4,520,113 5/1985 Gallo et al. .
4,629,783 12/1986 Cosand .................. 530/324

FOREIGN PATENT DOCUMENTS 0173529 3/1986 European Pat. Off. ............. 435/5
0201716 11/1986 European Pat. Off. ............. 435/5
85/04903 11/1985 PCT Int'l Appl. ................... 435/5

OTHER PUBLICATIONS

Ratner et al., Nature, 313, (1/24/85), pp. 277–284.
Schüpbach et al., New England Journal of Medicine, 312, (1/31/85), 265–270.
Sanchez-Pescador et al., Science, 227, (2/1/85), 484–92.
Shaw et al., Science, 226, (12/7/84), 1165–71.
Kalyanaraman, V. S. et al., Science, 225, 321–323.
Sarngadharan et al., Science, 224, 506–508, (1984).

Primary Examiner—Christine M. Nucker
Attorney, Agent, or Firm—Hamilton, Brook, Smith & Reynolds

[57] ABSTRACT

Gene segments of human T cell lymphotropic virus type III (HTLV-III) were expressed in *E. coli* as peptides that are reactive with sera from patients with acquired immune deficiency syndrome (AIDS). Among recombinant peptides one designated HTLV-III polypeptide 121, contained 85 amino acid residues encoded by a gene segment in the env-lor region of the HTLV-III genome. The polypeptide is strongly reactive with AIDS patient sera. The peptide produced and purified as a fusion protein on a large scale. Solid phase immunoassays employing this recombinant peptide as an immunoabsorbent can reliably and reproducibly detect antibodies in sera of patients with HTLV-III infection. In two representative serum panels, the assay detected the presence of antibodies in 120 of 121 sera from patients with AIDS or AIDS-related complex (ARC), and only in 1 of 92 normal controls. Based upon HTLV-III polypeptide 121 as immunoreactive agent, sensitive and specific immunoassays for HTLV-III infection have been developed.

15 Claims, 2 Drawing Sheets

IMMUNOCHEMICAL METHODS FOR THE DETECTION OF ANTIBODY AGAINST HTLV-III

DESCRIPTION

FIELD OF THE INVENTION

This invention is in the fields of immunology and virology.

BACKGROUND OF THE INVENTION

Human T cell lymphotropic virus-type III (HTLV-III) has been isolated from many patients with acquired immunodeficiency syndrome (AIDS). More than a hundred isolates have been obtained and although genetic variants with different restriction enzyme restriction maps have been observed sera from more than 90% of patients with AIDS or AIDS-related complex (ARC) contain antibodies reactive with the prototype isolate H9/HTLV-III-82. J. Schupbach et al. *Science* 224, 503 (1984); M. G. Aarngadharan et al. *Science* 224, 506 (1984). This not only suggests that HTLV-III is the causative agent of AIDS but also indicates that the anti-HTLV-III antibodies are highly crossreactive with the various genetic variants of the virus.

Groups reported to be at greatest risk of contracting AIDS include homosexual or bisexual males; intravenous drug users and recent Haitian immigrants to the United States. Hemophiliacs who receive blood products pooled from donors and recipients of multiple blood transfusions are also at risk. Clinical manifestations of AIDS include severe immune deficiency which generally involves a depletion of helper T lymphocytes, various opportunistic infections and Kaposi sarcoma. These may be accompanied by malignancies and infections. All AIDS patients die within 2-3 years of diagnosis. ARC patients may exhibit lymphadenopathy and depressed helper T cell counts; there is not, however, the devastating illness characteristic of full-blown AIDS. It is not now possible to predict who among them will develop the more serious symptoms.

Much of the evidence implicates HTLV-III as the etiological agent of the infectious AIDS. First, there is consistent epidemiology; greater than 80% of the patients with AIDS have antibodies specific for HTLV-III as revealed by Western blot analysis and solid phase immunoassays. Second, there has been reproducible identification and isolation of virus in this disease; as mentioned, more than 100 variants of HTLV-III have been isolated from AIDS patients. Third, there has been transmission of the disease to normal healthy individuals who received blood transfusions from infected blood donors.

Since the identification of HTLV-III as the probable cause of infectious AIDS and the establishment of a permissive T cell line for mass production of the virus, substantial progress has been made in characterizing the virus and in developing of diagnostic methods for the detection of HTLV-III infection. Most notable is the development of solid-phase immunoassays employing inactivated HTLV-III as a whole virus antigen immunoadsorbent for the detection of antibodies against HTLV-III in sera of patients. Such assays have been shown to detect antibodies in more than 80% of sera from patients with AIDS or ARC, or from individuals infected with HTLV-III and thus are useful for diagnosing AIDS and for screening contaminated blood.

Assays employing the whole virus, however, have several drawbacks. Large quantities of the virus must be cultivated as supply for test reagents. Although rigorous safety measures can be instituted, there are dangers associated with large scale cultivation of the infectious virus. Further, there exists a risk, however small, that test reagents prepared with the inactivated virus can be contaminated with live virus. Thus, persons who handle the reagents may be subjected to the risk of HTLV-III infection.

DISCLOSURE OF THE INVENTION

This invention pertains to immunochemical assays for detecting antibodies against HTLV-III employing an HTLV-III antigenic polypeptide produced by recombinant DNA methodology. The HTLV-III antigen, designated HTLV-III polypeptide 121, contains 83 amino acids and is probably derived from a viral envelope protein. Immunochemical assays utilizing the peptide are highly sensitive, specific and reproducible. The assays are an alternative to assays based on the whole virus which are equivalent, if not superior, in performance. The assays can be used to screen blood or other bodily fluids for presence of HTLV-III and to diagnose AIDS.

HTLV-III polypeptide 121 was identified by a shot gun cloning technique in which fragments of the HTLV-III genome were randomly cloned as fused genes into *E. coli* and expressed as a tripartite fusion protein which was strongly immunoreactive with AIDS patient sera. The HTLV-III DNA segment of the fused gene was sequenced and based upon this information, the amino acid sequence of the HTLV-III derived portion of the fusion protein (polypeptide 121) was assigned. The polypeptide was later determined to be encoded by a segment of the env-lor region of the HTLV-III genome (nucleotides 7259 - 7503). The polypeptide 121 DNA segment was re-engineered into a beta-glucuronidase vector and was expressed in *E. coli* at levels of up to 5% of total cellular protein as a different tripartite fusion protein consisting of 41 amino acids of *E. coli*, the 83 amino acid residues of the HTLV-III polypeptide 121 and 14 amino acids residues encoded by the nucleotides forming a multiple cloning site of the cloning vector. This fusion protein was purified to homogeneity by a three-step fractionation procedure and examined for reactivity with anti-HLTV-III antibody.

Immunoassays employing the recombinant peptide as the immunoreactive agent reliably and reproducibly detected anti-HTLV-III antibody in sera of patients with HTLV-III infection. In two representative serum panels, anti-HTLV-III antibody was detected in 99% (120/121) of sera from patients with AIDS and only in 1 of 92 normal controls. Because the peptide is a defined, single component, better homogeneity and less variability can be achieved than with the disrupted virus, giving rise to less background immunoreactivity in immunoassays based upon the polypeptide. As a result, fewer false positive results are generated.

HTLV-III polypeptide 121 can be biosynthesized by genetic engineering techniques either as the 85 amino acid residue peptide or as a part of a larger fused polypeptide containing exogenous peptide elements at its N-terminal and C-terminal. DNA segments which encode polypeptide 121 can be isolated from the viral genome or synthesized chemically. The polypeptide can be synthesized chemically by techniques of organic protein synthesis.

The polypeptide can be used in assays of various types including immunometric assays and antigen-sandwich assays. A preferred type of assay is a solid phase immunometric (double antibody) assay. HTLV-III polypeptide 121 is immobilized by attaching it to solid phase to form an antigen immunoadsorbent. The immunoadsorbent is used to adsorb anti-HTLV-III antibody from a sample of the biological fluid. The adsorbed anti-HTLV-III antibody is detected with an anti-(human IgG) antibody which is labeled radioisotopically, enzymatically, fluorometrically or in other ways. This second antibody, directed generally against human IgG, binds to anti-HTLV-III antibody adsorbed to the immunoadsorbent and produces a detectable signal which can be evaluated as an indication of the presence of anti-HTLV-III antibody in the sample.

The immunochemical assays employing HTLV-III polypeptide 121 provide several advantages over those based on the whole virus. Assays based upon HTLV-III polypeptide 121 eliminate the need to grow large quantity of the infectious virus. This alleviates the risk associated with this process. Additionally, assay reagents based upon the HTLV-III antigen rather than the whole virus will help mitigate the real or perceived risk of contracting AIDS by technicians who perform the assay.

In performance, assays employing HTLV-III polypeptide 121 are excellent. HLTV-III polypeptide 121 is a single, well defined component which provides a reproducible assay exhibiting less variability. For example, in solid phase assays, background label associated with the immunoadsorbent is low. Further, the assays are surprisingly highly sensitive and specific. Because the polypeptide presumably exhibits far fewer epitopes than the whole virus and consequently should be reactive with a smaller fraction of the antibody against the virion, the high sensitivity and specificity was not expected. In the immunometric assay, the polypeptide detected the presence of anti-HTLV-III antibody in 99% of sera of patients with AIDS and ARC. The very high specificity of the assay suggests that HTLV-III polypeptide 121 is derived from a highly antigenic portion of the virion and that antibody against the antigen is evoked in virtually all instances of HTLV-III infection. These performance characteristics provide for highly accurate screening of blood and other bodily fluids for the presence of HTLV-III and for greater precision in the diagnosis of AIDS.

Because of the apparent strong antigenicity of HTLV-III polypeptide 121, it could be used as a vaccine against the virus.

BEST MODE OF CARRYING OUT THE INVENTION

HTLV-III polypeptide 121 was expressed and identified by a shotgun cloning procedure. This procedure is described in detail in U.S. patent spplication Ser. No. 659,339, which is incorporated by reference herein. For completeness, the procedure is outlined here and described in further detail in the Exemplification Section below.

Cloned HTLV-III DNA was broken into fragments of approximately 500 base pairs in length and inserted into the "open reading frame" (ORF) cloning and expression vector pMR100. The inserted DNA was expressed in E. coli transformants as tripartite fusion proteins, consisting of an HTLV-III polypeptide fused to λCI protein at its N-terminal and beta-galactosidase at its C-terminal. About 300 clones were found to express beta-galactosidase activity indicating expression of the tripartite fusion proteins. AIDS patient sera containing anti-HTLV-III antibodies were used to screen for fusion proteins that were immunoreactive. Among twenty clones which produced proteins reactive with the AIDS sera, one clone, designated clone #121, expressed a fusion protein which was immunoreactive with all AIDS patient sera examined (24/24). The highly immunoreative protein produced by this clone was selected for further study.

The HTLV-III DNA segment of clone 121 was excised from pMR100 and sequenced by the Sanger technique. The nucleotide sequence is as follows:

```
ATT  GAG  GCG  CAA  CAG  CAT  CTG  TTG  CAA  CTC  ACA  GTC  TGG
GGC  ATC  AAG  CAG  CTC  CAG  GCA  AGA  ATC  CTG  GCT  GTG  GAA
AGA  TAC  CTA  AAG  GAT  CAA  CAG  CTC  CTG  GGG  ATT  TGG  GGT
TGC  TCT  GGA  AAA  CTC  ATT  TGC  ACC  ACT  GCT  GTG  CCT  TGG
AAT  GCT  ACT  TGG  AGT  AAT  AAA  TCT  CTG  GAA  CAG  ATT  TGG
AAT  AAC  ATG  ACC  TGG  ATG  GAG  TGG  GAC  AGA  GAA  ATT  AAC
AAT  TAC  ACA  AGC  TTA
```

Based upon the DNA sequence, the putative amino acid sequence of the HTLV-III polypeptide could be assigned. This sequence is given below.

```
Ile  Glu  Ala  Gln  Gln  His  Leu  Leu  Gln  Leu
Thr  Val  Trp  Gly  Ile  Lys  Gln  Leu  Gln  Ala
Arg  Ile  Leu  Ala  Val  Glu  Arg  Tyr  Leu  Lys
Asp  Gln  Gln  Leu  Leu  Gly  Ile  Trp  Gly  Cys
Ser  Gly  Lys  Leu  Ile  Cys  Thr  Thr  Ala  Val
Pro  Trp  Asn  Ala  Ser  Trp  Ser  Asn  Lys  Ser
Leu  Glu  Gln  Ile  Trp  Asn  Asn  Met  Thr  Trp
Met  Glu  Trp  Asp  Arg  Glu  Ile  Asn  Asn  Tyr
Thr  Ser  Leu
```

The pMR100 tripartite fusion protein synthesized by clone 121 was difficult to purify in sufficient quantity for sera screening because the expression level was low (approximately 1.0% of total cellular protein) and the protein was insoluble in conventional extractive buffer (probably due to the existence of 23 half-cystine residues). In order to enhance expression the HTLV-III polypeptide in E. coli the HTLV-III segment of clone 121 was cloned into a beta-glucuronidase expression vector. E. coli transformed with the recombinant vector expressed a 15 Kd fusion protein with short fusion partners at both ends (41 amino acids of E. coli. the 83 amino acid residues encoding by HTLV-III polypeptide and 13 amino acid residues encoded by a multiple cloning site of the vector). The amino acid sequence of the fusion protein is:

| Leu | Arg | Pro | Val | Glu | Thr | Pro | Thr | Arg | Glu |
|-----|-----|-----|-----|-----|-----|-----|-----|-----|-----|
| Ile | Lys | Lys | Leu | Asp | Gly | Leu | Trp | Ala | Phe |
| Ser | Leu | Asp | Arg | Glu | Asn | Cys | Gly | Ile | Asp |
| Gln | Ala | Ser | Ala | Val | Asp | Ala | Cys | Gly | Ser |
| Pro |     |     |     |     |     |     |     |     |     |
| Ile | Glu | Ala | Gln | Gln | His | Leu | Leu | Gln | Leu |
| Thr | Val | Trp | Gly | Ile | Lys | Gln | Leu | Gln | Ala |
| Arg | Ile | Leu | Ala | Val | Glu | Arg | Tyr | Leu | Lys |
| Asp | Gln | Gln | Leu | Leu | Gly | Ile | Trp | Gly | Cys |
| Ser | Gly | Lys | Leu | Ile | Cys | Thr | Thr | Ala | Val |
| Pro | Trp | Asn | Ala | Ser | Trp | Ser | Asn | Lys | Ser |
| Leu | Glu | Gln | Ile | Trp | Asn | Asn | Met | Thr | Trp |
| Met | Glu | Trp | Asp | Arg | Glu | Ile | Asn | Asn | Tyr |
| Thr | Ser | Leu |     |     |     |     |     |     |     |
| Leu | Lys | Thr | Lys | Gly | Pro | Arg | Asp | Thr | Pro |
| Ile | Phe | Ile | Gly |     |     |     |     |     |     |

Because of the insolubility of this fusion protein in non-denaturant buffers, a unique approach was taken to purify it. The purification procedure is described in U.S. patent application Ser. No. 707,076, entitled "A Method of Purifying Recombinant Proteins", filed concurrently herewith. The procedure entails three steps. First, about 75% soluble cellular protein was removed from *E. coli* cell lysates with a non-denaturant buffer (50 mM Tris HCl, pH 7.6, 5 mM EDTA and 0.1 mM phenyl methyl sulphonyl fluoride). The fusion protein was contained in the insoluble cell pellet at approximately 20% purity. The fusion protein was then solubilized under extreme denaturing conditions (8M urea or 6M guanidine HCl). The pellet was suspended in a denaturing, extraction buffer containing 8M Urea and 10 mM dithiothreitol (DTT). DTT is a reducing agent which was added to prevent the formation of intra- and intermolecular disulfide bridges by the 6 half cystine residues of the HTLV-III peptide. The suspension was homogenized and then centrifuged. In the final step, the supernatant containing the solubilized fusion protein was purified by ion exchange or gel filtration chromatography in 8M Urea and 10 mM DTT. The resultant product was chemically pure (98% by weight) and immunoreactively pure as judged by Western blot analysis.

The purified HTLV-III polypeptide 121 was evaluated for its ability to detect anti-HTLV-III antibody in AIDS and ARC patient sera.

HTLV-III polypeptide 121 was compared to HTLV-III as an antigen immunoadsorbent for anti-HTLV-III antibody. The polypeptide (0.2 μg) and the virus (at the maximal amount coatable) were coated onto wells of polyvinyl chloride plates. Serum sample was incubated in the well and $^{125}$I-goat-anti-(human IgG F$_c$) antibody was used to assess adsorbed anti-HLTV-III antibody. For all samples tested, the amount of label associated with the HTLV-III polypeptide 121 immunoadsorbent was greater than with the inactivated virus immunoadsorbent. These results suggest that even though the immunoadsorbent employing purified recombinant HTLV-III peptide may absorb only a specific fraction of the antibodies against HTLV-III in sera of AIDS patient (i.e. only those directed against the epitopes of this particular viral antigen), it probably has the capacity to adsorb all or most of the antibodies specific for it. The immunoadsorbent with the disrupted virus probably can absorb antibodies reactive with most virion proteins. However, probably due to the steric hindrance of dominant antigenic determinants, the loss of antigenicity during virus purification or the insufficiency of certain viral components on the solid phase, it can adsorb only a portion of the antibodies. The polypeptide 121 immunoassay gave rise to less background immunoreactivity than assay employing the whole virus. This is probably because HTLV-III polypeptide 121 as a more defined, single component, is more homogeneous and a less variable reagent than the whole virus.

Next, the solid phase assay was used to analyze panels of serum samples from patients with AIDS or ARC, from other high risk individuals, and from healthy normal controls. The assay detected anti-HTLV-III antibody in sera of 120 out of 121 patients with AIDS or ARC. Among the clinically healthy individuals who were either homosexual males or who had sexual contact with AIDS patients, the immunoassay detected all of those who had been shown to be positive by a Western blot analysis. In fact, many of AIDS and ARC sera, which demonstrated undetectable or marginal reactivity in Western blot analysis, were clearly positive in the immunoassay. The single AIDS serum missed by the immunoassay did not show an immunoreactive band in Western blot analysis. Among 92 sera of normal healthy controls, only 1 was slightly above background level. This particular serum did not show an immunoreactive band by Western blot analysis.

The very high specificity and sensitivity of HTLV-III polypeptide 121 in immunoassays for anti-HTLV-III antibody is a surprising phenomenon. The polypeptide displays far fewer epitopes than the whole virus, yet it is reactive with 99% of AIDS and ARC patent sera and at very low concentrations it can detect anti-HTLV-III antibody. Because of the small numbers of epitope relative to the whole virus, the polypeptide would be expected to exhibit lower specificity because the fraction of anti-HTL-VIII antibody reactive with it should be smaller than the fraction reactive with the whole virus and thus be less sensitive and specific. The unexpectedly high specificity may be explained by potent antigenicity of the polypeptide. It appears that in virtually all cases of HTLV-III infection antibody against polypeptide 121 (or the corresponding naturally occurring form of the antigen) are elicited.

When the DNA sequence of the HTLV-III genome was deciphered, (see U.S. patent application Ser. No. 659,339 filed on Jan. 23, 1985), the gene segment encoding HTLV-III polypeptide 121 was localized in a portion of the env-lor region of the genome. This indicates that polypeptide 121 is probably a part of the P160 and P41 viral proteins which are believed to be capsid proteins.

Identification of the HTLV-III gene segment which encodes polypeptide 121 and determination of the amino acid sequence of the polypeptide opens the way to several techniques for producing the polypeptide. Recombinant DNA techniques, including those described herein and others, may be used to produce the polypeptide. HTLV-III now can be routinely and reproducibly isolated from patients with AIDS and propagated in a line of permissive T cells developed for this purpose. M. Popovic et al. Science 224, 497 (1984); R. C. Gallo et al. Science 224, 500 (1984). From such cells HTLV-III proviral DNA can be obtained and cloned. Polypeptide 121 coding region of the HTLV-III genome which has been identified can be excised from the proviral DNA, inserted into an expression vector, preferably one which express the polypeptide at high levels, and expressed in transformed host cells.

Alternatively, DNA segments encoding HTLV-III polypeptide 121 can be synthesized chemically. Several techniques are available for synthesizing the DNA segment or equivalents.

HTLV-III polypeptide 121 is a part of the naturally occurring form of an HTLV-III antigen. Thus, the gene which encodes the entire antigen probably encompasses or overlaps the identified polypeptide 121 sequence. This gene can be cloned as expressed and the product may display equivalent or even superior reactivity with AIDS patient sera. In addition, other segments of HTLV-III DNA which encompass the polypeptide coding region or those which overlap this region and DNA segments which are modified by deletion, insertion or substitution of nucleotides may also yield HTLV-III polypeptides which exhibit the immunological properties of polypeptide 121. The term HTLV-III polypeptide 121 is inclusive of all of these different forms of the antigen.

In addition to genetic engineering techniques for synthesizing polypeptide 121 or its equivalents, the polypeptide can be synthesized directly by procedures of chemical protein synthesis. For example, polypeptide 121 can be synthesized by the solid phase procedure of Merrifield. As in the biosynthesis of the polypeptide, modified polypeptides can be synthesized chemically which are immunologically equivaent to HTLV-III polypeptide 121. For example, the polypeptide structure can be altered by addition, deletion or substitution of amino acid residues.

Immunochemical assays employing HTLV-III polypeptide 121 can take a variety of forms. The preferred type is a solid phase immunometric assay. In assays of this type, the HTLV-III polypeptide 121 is immobilized on a solid phase to form an antigenimmunoadsorbent. The immunoadsorbent is incubated with the sample to be tested. After an appropriate incubation period, the immunoadsorbent is separated from the sample and labeled anti-(human IgG) antibody is used to detect human anti-HTLV-III antibody bound to the immunoadsorbent. The amount of label associated with the immunoadsorbent can be compared to positive and negative controls to assess the presence or absence of anti-HTLV-III antibody.

The immunoadsorbent can be prepared by adsorbing or coupling purified HTLV-III polypeptide 121 to a solid phase. Various solid phases can be used, such as beads formed of glass, polystyrene, polypropylene, dextran or other material. Other suitable solid phases include tubes or plates formed from or coated with these materials.

Polypeptide 121 can be either covalently or noncovalently bound to the solid phase by techniques such as covalent bonding via an amide or ester linkage or adsorption. After the HTLV-III polypeptide is affixed to the solid phase, the solid phase can be post-coated with an animal protein, e.g., 3% fish gelatin. This provides a blocking protein which reduces nonspecific adsorption of protein to the immunoadsorbent surface.

The immunoadsorbent is then incubated with the sample to be tested for anti-HTLV-III antibody. In blood screening, blood plasma or serum is used. The plasma or serum is diluted with normal animal plasma or serum. The diluent plasma or serum is derived from the same animal species that is the source of the anti-(human IgG) antibody. The preferred anti-(human IgG) antibody is goat anti-(human IgG) antibody. Thus, in the preferred format, the diluent would be goat serum or plasma. The optimal dilution factor for human plasma and serum is about 10–11 fold.

The conditions of incubation, e.g. pH and temperature, and the duration of incubation are not crucial. These parameters can be optimized by routine experimentation. Generally, the incubation will be run for 1–2 hours at about 45° C. in a buffer of pH 7–8.

After incubation, the immunoadsorbent and the sample are separated. Separation can be accomplished by any conventional separation technique such as sedimentation or centrifugation. The immunoadsorbent then may be washed free of sample to eliminate any interfering substances.

The immunoadsorbent is incubated with the labeled anti-(human IgG) antibody (tracer) to detect human antibody bound thereto. Generally the immunoadsorbent is incubated with a solution of the labeled anti-(human IgG) antibody which contains a small amount (about 1%) of the serum or plasma of the animal species which serves as the source of the anti-(human IgG) antibody. Anti-(human IgG) antibody can be obtained from any animal source. However, goat anti-(human IgG) antibody is preferred. The anti-(human IgG) antibody can be an antibody against the $F_c$fragment of human IgG, for example, goat anti-(human IgG) $F_c$ antibody.

The anti-(human IgG) antibody or anti-(human IgG)$F_c$ can be labeled with a radioactive material such as $^{125}$Iodine; labeled with an optical label, such as a fluorescent material; or labeled with an enzyme such as horseradish peroxidase. The anti-human antibody can also be biotinylated and labeled avidin used to detect its binding to the immunoadsorbent.

After incubation with the labeled antibody, the immunoadsorbent is separated from the solution and the label associated with the immunoadsorbent is evaluated. Depending upon the choice of label, the evaluation can be done in a variety of ways. The label may be detected by a gamma counter if the label is a radioactive gamma emitter, or by a fluorimeter, if the label is a fluorescent material. In the case of an enzyme label detection may be done colorimetrically employing a substrate for the enzyme.

The amount of label associated with the immunoadsorbent is compared with positive and negative controls in order to determine the presence of anti-HTLV-III antibody. The controls are generally run concomitantly with the sample to be tested. A positive control is a serum containing antibody against HTLV-III; a negative control is a serum from healthy individuals which do not contain antibody against HTLV-III.

For convenience and standardization, reagents for the performance of the immunometric assay can be assembled in assay kits. A kit for screening blood, for example, can include:

(a) an immunoadsorbent e.g. a polystyrene bead coated with HTLV-III polypeptide 121;
(b) a diluent for the serum or plasma sample, e.g. normal goat serum or plasma;
(c) an anti-(human IgG) antibody e.g. goat anti-(human IgG) antibody in buffered, aqueous solution containing about 1% goat serum or plasma;
(d) a positive control i.e. serum containing antibody against polypeptide 121; and
(e) a negative control e.g. pooled sera from healthy individuals which does not contain antibody against polypeptide 121.

If the label is an enzyme, an additional element of the kit can be the substrate for the enzyme.

Another type of assay for anti-HTLV-III antibody is an antigen sandwich assay. In this assay, labeled HTLV-III polypeptide 121 is used in place of anti-(human IgG) antibody to detect anti-HTLV-III antibody bound to the immunoadsorbent. The assay is based in principle on the bivalency of antibody molecules. One binding site of the antibody binds the antigen affixed to the solid phase; the second is available for binding the labeled antigen. The assay procedure is essentially the same as described for the immunometric assay except that after incubation with the sample, the immunoadsorbent is incubated with a solution of labeled HTLV-III polypeptide 121. HTLV-III polypeptide can be labeled with radioisotope, an enzyme, etc. for this type of assay.

In a third format, the bacterial protein, Protein A, which binds the $F_c$ segment of an IgG molecule without interfering with the antigen-antibody interaction can be used as the labeled tracer to detect anti-HTLV-antibody adsorbed to the immunoadsorbent. Protein A can be readily labeled with a radioisotope, enzyme or other detectable species.

Immunochemical assays employing the HTLV-III polypeptide 121 have several advantages over those employing a whole (or disrupted) virus. For one, assays based upon the polypeptide will alleviate the concern over growing large quantities of infectious virus and the inherent variability associated with cell culturing and virus production. Further, the assay will help mitigate the real or perceived fear of contracting AIDS by technicians in hospitals, clinics and blood banks who perform the test. As mentioned, reagents for assays based upon the whole virus (e.g. whole virus antigen immunoadsorbent), even though they are made with a disrupted, inactivated virus, present a risk of contamination with live virus. For example, a possible source of live virus contamination may be residual cell debris from the virus isolation process. Although extensive precautions can be taken to reduce the risk of contamination, it is virtually impossible to completely eliminate it. Significantly, the risk, though minimal, may be perceived as greater than it actually is by persons who handle the test reagents. Assay reagents without whole virus can help minimize this perception of risk. HTLV-III polypeptide 121 immunoassays provide a substitute for assays based on the whole virus which are at least comparable in sensitivity and specificity and superior in reproducibility.

As mentioned, HTLV-III polypeptide 121 is apparently derived from a viral envelope protein which is highly antigenic. Because of this, the polypeptide may be a useful vaccine against the virus. For this purpose, vaccine compositions can be made containing immunogenic amounts of purified polypeptide 121 in a suitable vehicle.

The invention is illustrated further by the following Exemplification.

Exemplification

I. Expression of HTLV III polypeptide 121

HTLV-III DNA was excised from λBH-10, a recombinant λ phage containing a 9 Kb segment of HTLV-III DNA inserted into the vector λgtWES λB. See B. H. Haha et al. *Nature* 312, 166 (1984). The HTLV-III DNA was fragmented by sonication. DNA fragments of about 0.5 Kb in size were purified by gel electrophoresis. The purified fragments were end repaired, and cloned into the SmaI site of the open reading frame (ORF) plasmid vector, pMR100, developed by Gray, M. R. et al. *PNAS*, 79 6598 (1982). pMR100 contains a bacterial lac promoter DNA segment linked to a second DNA fragment containing a hybrid coding sequence in which the N-terminus (5'segment) of the CI gene of bacteriophage lambda is fused to an N-terminal-deleted lacIZ gene (3'segment). A short linker DNA fragment, containing a Sma I cloning site, has been inserted between these two fragments in such a manner that a frame shift mutation has been introduced upstream of the lacIZ coding DNA. As a result, pMR100 does not produce any detectable beta-galactosidase activity when introduced into Lac$^-$host (*E. coli*) LG90 cells. The insertion of foreign DNA containing an open reading frame, in this case the HTLV-III DNA, at the Sma I cloning site can reverse the frame shift mutation if the inserted coding sequence is in the correct reading frame with respect to both the λCI leader and the lacIZ gene. Transformants were screened on McConkey plates to detect individual clones that express beta-galactosidase enzymatic activity in situ. J. H. Miller, *Experiments in Molecular Genetics* (Cold Spring Harbor Laboratory, Cold Spring Harbor, N.Y., 1982).

Among 6000 ampicillin resistant *E. coli* LG90 transformants screened, about 300 were found to express beta-galactosidase activity. Colony hybridization using $^{32}$P-labelled nick-translated HTLV-III DNA as a probe revealed that all these Lac$^+$ clones contained HTLV-III DNA. In the Lac$^+$ clones the HTLV-III fragment inserted into the Sma I site of pMR100 must contain no stop codons in the reading frame set by the λCI leader segment and the lacIZ gene must also be in correct translational reading frame. The three-element-fused genes were expressed as tripartite fusion proteins, having a portion of the λCI protein at the N-terminus, the HTLV-III segment in the middle, and the lacIZ polypeptide at the C-terminus.

The proteins produced by the Lac$^+$ clones were analyzed by running cell lysates on 7.5% SDS-polyacrylamide gels along with those of the control Lac$^+$ clone pMR200, which produced a λCI-beta-galactosidase fusion protein. The lacIZ gene in pMR200 is identical to that in pMR100 except that it has a single base pair deletion which brings it in phase with the λCI gene to produce an active beta-galactosidase. By virtue of the very large size of the beta-galactosidase and its fusion proteins, they were separated from the bulk of proteins in the cell lysates on the SDS-polyacrylamide gels and could be easily identified by Commassie blue staining as some of the Lac$^+$ clones containing HTLV-III DNA produce polypeptides that are larger (15,000 to 27,000 daltons) than the λCI-lacIZ fusion protein. These findings are consistent with data that the DNA inserts are up to 700 bp long. The beta-galactosidase fusion proteins accounted for about 1-2% of total cellular protein.

The peptides produced by the Lac$^+$ clones were examined by Western blot analysis [H. Towbin et al. *PNAS USA*, 76, 4350 (1979)] for immunoreactivity with sera from AIDS patients. After the lysates of Lac$^+$ clones were electrophoresed in SDS-polyacrylamide gels, they were electro-transferred to nitrocellulose filters. The protein blots were first reacted with AIDS patient sera and then with $^{125}$I-labeled goat anti-human IgG. The recombinant peptides also reacted with anti-beta-galactosidase antiserum, consistent with the proposition that they had the general tripartite structure λCI-HTLV-III peptide-LacIZ. From the immunoreactivity pattern of the negative controls, pMR100 and pMR200, which did not contain any HTLV-III DNA insert, it is evident that the particular AIDS serum contained antibodies reactive with several bacterial proteins of the host E. coli. This is not surprising, since AIDS patients are usually infected with a number of bacteria. Absorbing AIDS patient sera with Sepharose 4B conjugated with E. coli extract reduced the background immunoreactivity to some extent but did not completely eliminate it.

About 300 independent HTLV-III DNA-containing Lac+ colonies were analyzed in SDS polyacrylamide gels using Commassie blue staining and Western blotting. About half of them were found to express fusion proteins containing extra peptides of about 100–200 amino acids, corresponding to HTLV-III DNA inserts of 300–600 bp long. Of these fusion proteins 20 were found to react specifically with AIDS patient sera. The unreactive clones probably contain peptides that fold in such a way that they are not reactive with antibodies or contain peptides derived from epitopes of HTLV-III protein molecules which are not immunogenic in AIDS patients. The other half of the Lac+ clones expressed fusion proteins whose sizes were not obviously different from that of the λCI-beta-galactosidase protein. None of this group of fusion proteins was found to react with sera of AIDS patients.

The HTLV-III DNA inserts from Lac+ ORF clones were mapped to specific segments in the HTLV-III genome using Southern blotting procedures. In these studies, each plasmid clone was labeled with $^{32}P$ nick-translation and hybridized to a battery of HTLV-III DNA restriction fragments. This hybridization analysis mapped all of the Lac+ ORF clones into four open reading frame segments designated ORF-A, ORF-B, ORF-C, and ORF-D consistent with the DNA sequencing data. The open reading frames ORF-A and -B, corresponding to the coding regions of the gag and pol gene, are 1.5 Kb and 3.0 Kb long, respectively. ORF-C is about 0.6 Kb long, which slightly overlaps with the ORF-B region and is capable of encoding a polypeptide of 21 Kd. The location of ORF-C and its overlap with the pol gene are reminiscent of the structure of the env gene in HTLV-I and -II viruses. However, ORF-C, designated as the short open reading frame (sor), is too short to code for the entire envelope protein. The fourth open reading frame, ORF-D, is 2.5 Kb long and could encode a large precursor of the major envelope glycoprotein and another protein derived from the 3' terminus which may be analogous to the lor product of HTLV-I and -II. This region has been designated as env-lor (17). The region is at least twice as long as the lor of HTLV-I and HTLV-II and it is unclear at the present time whether single or multiple proteins are encoded therein.

By southern blot analysis the 20 Lac+ ORF clones expressing immunoreactive fusion proteins were mapped into ORF-A, ORF-B, or ORF-D, but not into the sor region.

Figure 1:
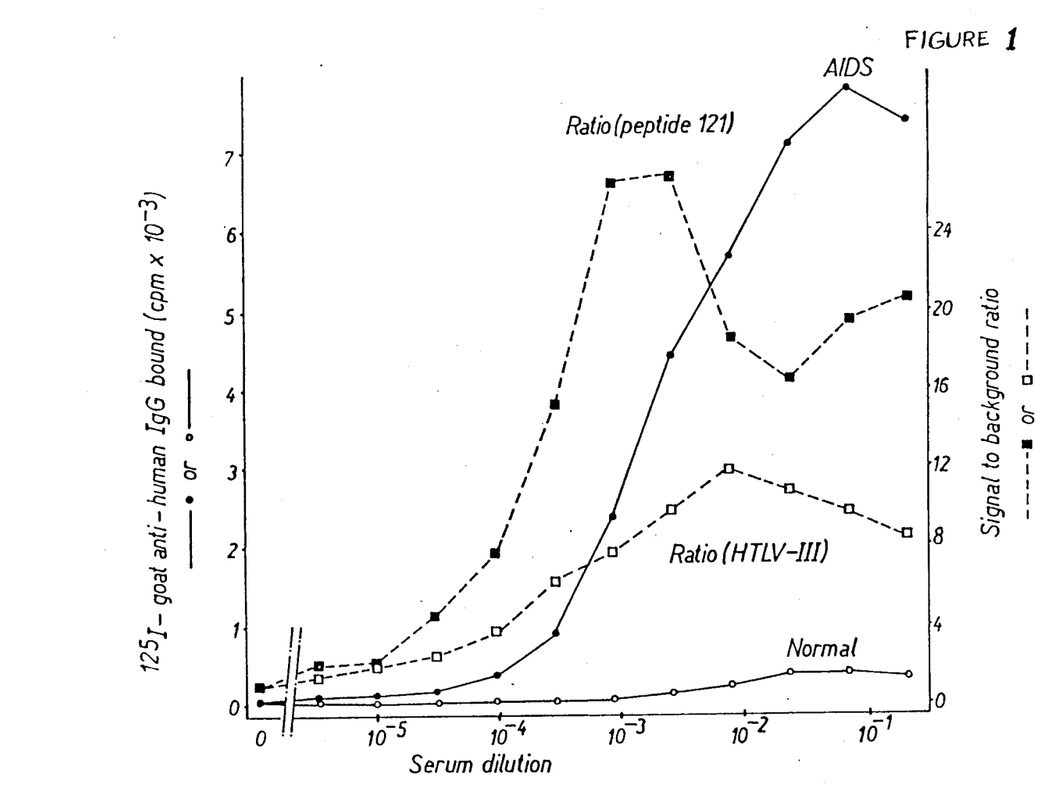
FIG. 1 is a comparison between solid phase immunoadsorbents using recombinant HTLV-III antigen, polypeptide 121, and inactivated, disrupted HTLV-III as antigen.

DNA sequencing analysis was also employed to locate the boundaries of HTLV-III inserts of several ORF clones. The results are summarized in FIG. 1B. Among these Lac+ clones which expressed immunoreactive peptides, ORF clones #113, 121, and 127 were particularly interesting because these DNA inserts were derived from the ORF-D, the env-lor region. Clone 121, which expressed a fusion protein reactive with all AIDS patient sera examined corresponded to a segment of the env-lor region from nucleotides 7259 to 7503 of the HTLV-III genome. The HTLV-III antigen expressed by this clone was selected for further study.

II. Purification and Characterization of HTLV III Polypeptide 121

The low level of expression of the fusion peptide in the pMR100 vector (1.0% of total cellular protein) and its insolubility (probably due to the existence 23 half-cystine residues) made it difficult to purify sufficient quantity of the peptide for sera screening. To express peptide at higher levels in E. coli, the fragment was cloned into a beta-glucuronidase expression vector.

The recombinant pMR100 vector containing the HTLV-III inserted was isolated from clone 121. The HTLV-III DNA was excised with a SmaI restriction endonuclease. The insert was separated by gel electrophoresis and identified by an HTLV-III DNA probe. The excised HTLV-III DNA was inserted in high expression beta-glucuronidase vector (Repligen, Boston, Mass.), and E. coli LG90 cells were transformed with the recombinant vector and cultured to allow expression of the fusion protein. This fusion protein consists of 31 amino acid residues of the E. coli, 83 amino acid residues encoded by the segment of the env-lor region of HTLV-III and 13 amino acid residues encoded by nucleotides forming a multiple cloning site of the vector. (See above for amino acid sequence.) The fusion protein was purified by the following procedure.

A. Solubilization of AIDS Peptide

Cells transformed with the vector harboring polypeptide 121 coding region were mechanically disrupted and lysed in Dyna-Mill ™ homogenizer using an extraction buffer, 50 mM Tris HCl, pH 7.6, 5 mM EDTA and 0.1 mM phenyl methyl sulphontyl fluoride. Cell lysates were centrifused at 12,000×g for 5 minutes at 4° C. SDS-polyacrylamide get analysis revealed that the resulting pellet contains all the HTLV-III polypeptide 121 at about 20% purity. Since supernatant contains about 90% of total cell protein, the expression of polypeptide 121 appears to be at level of 5% of total protein. To solubilize the polypeptide 121 from the pellet, extreme denaturing conditions (8M urea or 6M guanidine HCl) were necessary. The pellets were suspended in 10 volumes of extraction buffer containing 8M urea and homogenized using a POLYTRON ™ homogenizer. The homogenized suspension was stirred for 1 hr at room temperature and centrifuged at 20k for overnight at 14° C. The resulting supernatant was used for further purification.

B. Ion-Exchange Chromatography

Since the polypeptide 121 contains 6 half cystine residues, it was anticipated that intermolecular disulfide bridges might be formed not only between polypeptide 121 but also between polypeptide 121 and E. coli protein containing half-cystines. To minimize formation of disulfide bridges, the reducing agent dithiothreitol (DTT) was included in buffers used in the ion-exchange chromatography.

The urea extract of cell lysate pellet solution (16.5 ml) in 8M urea was adjusted to pH 8.0 with 5M NaO and incubated with 30 mg of DTT for 1 hr at 45° C. to reduce all possible disulfide bridges. This solution was applied on to a DEAE-Sepharose-Fast Flow ™ column (1.6×17 cm) equilibrated with the buffer containing 50 mM Tris HCl, pH 8.5, 10 mM DTT and 8M urea. Polypeptide 121 was eluted isocratically in the third peak monitored by UV absorbency at 280 nm. The peptide was more than 98% pure as judged by SDS-polyacrylamide gel electrophoresis.

This chromatographically purified AIDS peptide remained in solution after exhaustive dialysis against 50 mM Tris HCl buffer at pH 8.5 without 8M urea.

C. Gel Filtration Chromatography

Using the same reducing and denaturing conditions, the pellet solution in 8M urea was also applied to a gel filtration column, Sephacryl TM S-200. 5 ml of partially purified polypeptide 121 in buffer containing 50 mM Tris HCl, pH 8.5, 10 mM DTT in 8M urea was incubated at 45° C. for 30 minutes and applied on a column of Sephacryl TM S-200 (2.6×35 cm) equilibrated in the same buffer. This process removed contaminants of higher molecular weight than the recombinant polypeptide 121 but not the lower molecular weight contaminants thereby producing about 85% pure peptide.

Immune Reactivity to AIDS Sera

In Western blotting analysis employing peptide 121 on nitrocellulose strips and the pooled sera from AIDS patients as the source of antibodies only a single band was observed. $^{125}$I-goat anti human IgG Fc was used as the tracer to indicate the presence and amount of human antibodies specific for the viral antigens. The pooled sera contained antibodies against all major bands of viral components including P41 (segment of HTLV-III envelop protein) and P24 (an HTLV-III core protein) as indicated by Western blot analysis. Even though some patients' sera showed barely detectable P41 or any other bands in Western blot analysis with inactivated HTLV-III as the antigen, the produced strong bands with polypeptide 121 as the antigen.

HTLV-III peptide 121 was evaluated as an immunoadsorbent on plastic solid phase for immunoassays to quantitate anti-HTLV-III antibodies in patient sera and to compare the recombinant viral antigen with inactivated HTLV-III as solid phase immunoadsorbents. HTLV-III peptide 121 at 2 mg/ml in tris. HCl (0.05M, pH 8.0) was pipetted into PVC microtiter plate, 100 microliters per well. Purified HTLV-III preparation at 2 mg/ml was added NP-40 at final concentration of 0.5% and then heated at 56° C. for 30 min. It was diluted with bicarbonate buffer (0.M, pH 9.6) to 4000 fold and then pipetted into wells, 100 microliters per well, of PVC microtiter plate. After incubation at 4° C. for 16 hours, the antigen solutions were removed, and the wells were washed three times with phosphate buffered saline (PBS). The wells were "post-coated" with 3% liquid gelatin in PBS for 2 hours and washed three times with PBS. 190 microliters of dilutant PBS buffer containing 20% goat serum and 1% gelatin was pipetted into each normal well and 10 microliters of serum samples were pipetted into the wells (1:20 dilution of serum). After 2 hours incubation at room temperature, the samples were removed and wells washed with PBS three times. 100,000 cpm of goat anti-human IgG Fc antibodies in 100 microliters were added into each well and the plates were incubated further for 1 h. After the plates were washed with water 3 times, the plates were dried and wells were cut and counted for $^{125}$I in a 'Y'-scintillation counter. As shown in FIG. 1, with the pooled AIDS patient sera as the positive serum sample and pooled sera from normal healthy individuals as the negative control, the immunoassay detected positive signal at serum dilutions down to 300,000 fold. Even though the pooled positive sera contained more antibodies against P24 than against P41 as revealed by Western blot analysis, the signal to background ratio exhibited with polypeptide 121 was larger than that with inactivated virus (FIG. 1).

These results suggest that even though the immunoadsorbent employing purified recombinant HTLV-III peptide may absorb only a specific fraction of the antibodies against HTLV-III in sera of AIDS patients, it probably provides the capability to absorb all or most of the antibodies specific for the particular peptide antigen. The immunoadsorbent with the disrupted virus probably can absorb antibodies reactive with most virion proteins, but probably due to the steric hindrance of dominant antigenic determinants, the loss of antigenicity during virus purification or the insufficiency of certain viral components on the solid phase, it can absorb only a portion of the antibodies. In addition, because the recombinant peptide is more defined than disrupted virus, better homogeneity and less variability can be achieved, giving rise to less background immunoreactivity in the immunoassays.

Figure 2:
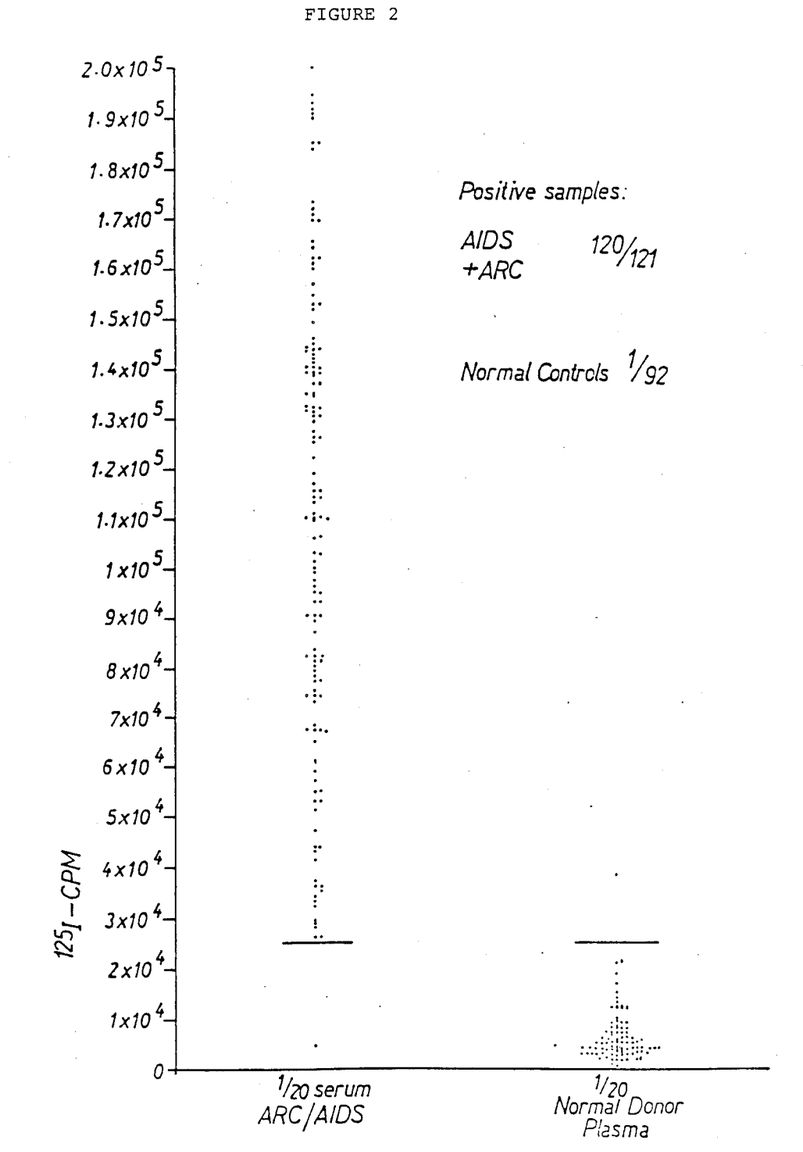
FIG. 2 shows assay results on sera samples from patients with AIDS or ARC and from normal individuals with immunoradiometric assays employing recombinant HTLV-III polypeptide 121 as a solid-phase immunoadsorbent.

Having characterized the basic parameters of the immunoradiometric assay with the recombinant peptide 121, panels of serum samples from patients with AIDS or ARC, from other high risk individuals, and from healthy normal controls were analyzed. As shown in Table 1 and FIG. 2, the assay detected 120 of 121 patients with AIDS or ARC. Among the clinically healthy individuals who were either homosexual males or who had sexual contact with AIDS patients, the immunoassay detected all of those who had been shown to be also positive by Western blot analysis. In fact, many of AIDS and ARC sera, which demonstrated undetectable or marginal reactivity in Western blot analysis, were clearly positive in the immunoassay. The only one AIDS serum missed by the immunoassay did not show immunoreactive band in Western blot analysis. Among 92 sera of normal healthy controls, only one was slightly above background level. This particular serum did not show an immnunoreactive band by Western blot analysis.

TABLE 1

| Results of sera tested with an immunoassay employing a recombinant HTLV-III antigen peptide. | | | |
|---|---|---|---|
| Serum from | Total number tested | Western blot positive with HTLV-III virus | Immunoassay positive |
| Patients with AIDS | 121 | 116[1] | 120 |
| Individuals with sexual contact with AIDS patients | 6 | 4 | 4 |
| Healthy homosexual | 13 | 3 | 3 |
| Normal plasma donors | 92 | (2) | 1 |

[1]Two of the five negatives by Western blot analysis show very weak bands.
[2]Thirty five normals were analyzed by Western blot analysis and were all negative.

In summary, the present studies have demonstrated that solid-phase immunoassays employing a peptide encoded by a gene segment in the env-lor region of HTLV-III and Produced by genetic engineering method can be used to detect anti-HTLV-III antibodies in 99% of sera of patients with AIDS or ARC, or of individuals infected with HTLV-III. The immunometric assay is a quantitative one that can measure antibody over a very broad range. Because very defined, consistently homogeneous peptide can be produced in large quantities, the production of immunoassays with a peptide such as described herein offer certain advantages over the production of immunoassays with the inactivated, disrupted virus.

Equivalents

Those skilled in the art will recognize, or be able to ascertain, by no more than routine experimentation, many equivalents of the specific embodiments of the invention described herein. Such equivalents are intended to be encompassed by the following claims.

We claim:

1. An immunoreactive HTLV-III derived polypeptide comprising HTLV-III polypeptide 121 having the sequence

| Ile | Glu | Ala | Gln | Gln | His | Leu | Leu | Gln | Leu |
|-----|-----|-----|-----|-----|-----|-----|-----|-----|-----|
| Thr | Val | Trp | Gly | Ile | Lys | Gln | Leu | Gln | Ala |
| Arg | Ile | Leu | Ala | Val | Glu | Arg | Tyr | Leu | Lys |
| Asp | Gln | Gln | Leu | Leu | Gly | Ile | Trp | Gly | Cys |
| Ser | Gly | Lys | Leu | Ile | Cys | Thr | Thr | Ala | Val |
| Pro | Trp | Asn | Ala | Ser | Trp | Ser | Asn | Lys | Ser |
| Leu | Glu | Gln | Ile | Trp | Asn | Asn | Met | Thr | Trp |
| Met | Glu | Trp | Asp | Arg | Glu | Ile | Asn | Asn | Tyr |
| Thr | Ser | Leu |     |     |     |     |     |     |     |

2. In an immunochemical assay for detecting or quantifying antibody against HTLV-III in a fluid comprising contacting the fluid with an immunoreactive HTLV-III-derived antigen under conditions which allow the antigen to bind anti-HTLV-III antibody in the fluid, the improvement wherein the immunoreactive HTLV-III-derived polypeptide comprises HTLV-III polypeptide 121 having the sequence

| Ile | Glu | Ala | Gln | Gln | His | Leu | Leu | Gln | Leu |
|-----|-----|-----|-----|-----|-----|-----|-----|-----|-----|
| Thr | Val | Trp | Gly | Ile | Lys | Gln | Leu | Gln | Ala |
| Arg | Ile | Leu | Ala | Val | Glu | Arg | Tyr | Leu | Lys |
| Asp | Gln | Gln | Leu | Leu | Gly | Ile | Trp | Gly | Cys |
| Ser | Gly | Lys | Leu | Ile | Cys | Thr | Thr | Ala | Val |
| Pro | Trp | Asn | Ala | Ser | Trp | Ser | Asn | Lys | Ser |
| Leu | Glu | Gln | Ile | Trp | Asn | Asn | Met | Thr | Trp |
| Met | Glu | Trp | Asp | Arg | Glu | Ile | Asn | Asn | Tyr |
| Thr | Ser | Leu |     |     |     |     |     |     |     |

3. A method of detecting antibody against HTLV-III in a biologial fluid, comprising the steps of:
   (a) incubating an immunoadsorbent comprising a solid phase to which is attached an immunoreactive HTLV-III derived polypeptide comprising HTLV-III polypeptide 121 having the amino acid sequence

| Ile | Glu | Ala | Gln | Gln | His | Leu | Leu | Gln | Leu |
|-----|-----|-----|-----|-----|-----|-----|-----|-----|-----|
| Thr | Val | Trp | Gly | Ile | Lys | Gln | Leu | Gln | Ala |
| Arg | Ile | Leu | Ala | Val | Glu | Arg | Tyr | Leu | Lys |
| Asp | Gln | Gln | Leu | Leu | Gly | Ile | Trp | Gly | Cys |
| Ser | Gly | Lys | Leu | Ile | Cys | Thr | Thr | Ala | Val |
| Pro | Trp | Asn | Ala | Ser | Trp | Ser | Asn | Lys | Ser |
| Leu | Glu | Gln | Ile | Trp | Asn | Asn | Met | Thr | Trp |
| Met | Glu | Trp | Asp | Arg | Glu | Ile | Asn | Asn | Tyr |
| Thr | Ser | Leu |     |     |     |     |     |     |     | with a sample of the biological fluid to be tested, under conditions which allow anti-HTLV-III antibody in the sample to bind to the immunoadsorbent;
   (b) separating the immunoadsorbent from the sample; and
   (c) determining if antibody has bound to the immunoadsorbent as an indication of anti-HTLV-III in the sample.

4. A method of claim 3, wherein the step (c) of determining if antibody has bound to the immunoadsorbent comprises incubating the immunoadsorbent with a labeled antibody against antibody of the species from which the biological fluid is derived; separating the immunoadsorbent from the labeled antibody after the incubation period; and detecting the label associated with the immunoadsorbent as an indication of antibody bound to the immunoadsorbent.

5. A method of claim 3, wherein the step c of determining if antibody has bound to the immunoadsorbent comprises incubating the immunoadsorbent with laeled HTLV-III polypeptide 121; separating the immunoadsorbent from the labeled HTLV-III polypeptide 121; and detecting the label associated with the immunoadsorbent as an indication of antibody bound to the immunoadsorbent.

6. A method of claim 3, wherein the step c of determining if antibody has bound to the immunoadsorbent comprises incubating the immunoadsorbent with labeled Proten A; separating the immunoadsorbent from the labeled Protein A; and detecting the label associated with the immunoadsorbent as an indication of antibody bound to the immunoadsorbent.

7. A method of detecting antibody against HTLV-III in a human serum or plasma sample, comprising the steps of:
   (a) providing an immunoadsorbent comprising a bead coated with an immunoreactive HTLV-III derived polypeptide comprising of HTLV-III polypeptide 121 having the amino acid sequence

| Ile | Glu | Ala | Gln | Gln | His | Leu | Leu | Gln | Leu |
|-----|-----|-----|-----|-----|-----|-----|-----|-----|-----|
| Thr | Val | Trp | Gly | Ile | Lys | Gln | Leu | Gln | Ala |
| Arg | Ile | Leu | Ala | Val | Glu | Arg | Tyr | Leu | Lys |
| Asp | Gln | Gln | Leu | Leu | Gly | Ile | Trp | Gly | Cys |
| Ser | Glyc | Lys | Leu | Ile | Cys | Thr | Thr | Ala | Val |
| Pro | Trp | Asn | Ala | Ser | Trp | Ser | Asn | Lys | Ser |
| Leu | Glu | Gln | Ile | Trp | Asn | Asn | Met | Thr | Trp |
| Met | Glu | Trp | Asp | Arg | Glu | Ile | Asn | Asn | Tyr |
| Thr | Ser | Leu |     |     |     |     |     |     |     | with a sample of the human serum or plasma sample to be tested, under conditions which allow anti-HTLV antibody in the sample to bind to the immunoadsorbent;
   (b) separating the immunoadsorbent from the sample; and
   (c) determining if antibody has bound to the immunoadsorbent as an indication of anti-HTLV-III in the sample.

8. A method of claim 7, wherein the immunoabsorbent further comprises a coat of animal protein.

9. A method of claim 7, wherein the labeled anti-(human IgG) antibody is an animal antibody and the serum or plasma sample is diluted with normal serum of an animal of the same species.

10. A method of claim 9, wherein the anti-(human IgG) antibody is a goat antibody and the serum or plasma sample is diluted with normal goat serum.

11. A method of claim 7, wherein the anti-(human IgG) antibody is labeled with a radioisotope, an enzyme or a fluorescent compound.

12. An immunoadsorbent for use in a solid phase immunochemical assay for antibody against HTLV-III, comprising a solid phase to which is affixed an immunoreactive HTLV-III polypeptide comprising polypeptide 121 having the sequence:

| | | | | | | | | | |
|---|---|---|---|---|---|---|---|---

UNITED STATES PATENT AND TRADEMARK OFFICE
CERTIFICATE OF CORRECTION

PATENT NO. : 4,774,175

DATED : September 27, 1988

INVENTOR(S) : Tse W. Chang, Ikunoshin Kato, Pranab Chanda, Nancy T. Chang, Scott Putney It is certified that error appears in the above-identified patent and that said Letters Patent is hereby corrected as shown below:

On the title page ([75] Inventors:), after "Pa.", insert ---; Scott D. Putney, Arlington, Ma.---

On the title page ([73] Assignee:), after "Pa.", insert ---Repligen Corporation, Cambridge, Ma.---

Signed and Sealed this

Seventh Day of February, 1989

*Attest:*

DONALD J. QUIGG

*Attesting Officer*  *Commissioner of Patents and Trademarks*